US010648110B2

(12) United States Patent
Kramkowski et al.

(10) Patent No.: US 10,648,110 B2
(45) Date of Patent: May 12, 2020

(54) CARDED NONWOVEN FIBROUS WEB AND USE IN ABSORBENT ARTICLES

(71) Applicant: The Procter & Gamble Company, Cincinnati, OH (US)

(72) Inventors: Silke Kramkowski, Schwalbach am Taunus (DE); Ekaterina Ponomarenko, Schwalbach am Taunus (DE); Adele Bruell, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 467 days.

(21) Appl. No.: 15/442,802

(22) Filed: Feb. 27, 2017

(65) Prior Publication Data

US 2017/0260689 A1 Sep. 14, 2017

(30) Foreign Application Priority Data

Mar. 8, 2016 (EP) .................................... 16159074

(51) Int. Cl.
| | |
|---|---|
| *D04H 1/541* | (2012.01) |
| *A61F 13/51* | (2006.01) |
| *A61F 13/15* | (2006.01) |
| *A61F 13/537* | (2006.01) |
| *A61F 13/53* | (2006.01) |

(52) U.S. Cl.
CPC ....... *D04H 1/541* (2013.01); *A61F 13/15642* (2013.01); *A61F 13/51* (2013.01); *A61F 13/53747* (2013.01); *A61F 2013/530226* (2013.01); *D10B 2509/026* (2013.01)

(58) Field of Classification Search
CPC ..... A61F 13/15617–15658; A61F 2013/53024
See application file for complete search history.

(56) References Cited

U.S. PATENT DOCUMENTS

| | | | |
|---|---|---|---|
| 5,773,120 A | 6/1998 | Deka et al. | |
| 6,383,958 B1 | 5/2002 | Swanson et al. | |
| 6,610,898 B1* | 8/2003 | Magnusson | ....... A61F 13/53747 604/365 |
| 7,695,660 B2* | 4/2010 | Berrigan | .............. D01D 5/0985 156/160 |
| 7,786,341 B2* | 8/2010 | Schneider | ............. A61F 13/537 604/367 |
| 2001/0027302 A1* | 10/2001 | Glaug | ............... A61F 13/53747 604/378 |
| 2002/0009937 A1* | 1/2002 | Dukes | ........................ C08J 3/03 442/156 |
| 2002/0119720 A1* | 8/2002 | Arora | ................ A61F 13/15707 442/327 |
| 2002/0177378 A1 | 11/2002 | Bodaghi | |

(Continued)

OTHER PUBLICATIONS

International Search Report and Written Opinion, PCT/US2017/020337, dated May 17, 2017.

*Primary Examiner* — Susan S Su

(74) *Attorney, Agent, or Firm* — Christian M. Best

(57) ABSTRACT

A carded nonwoven fibrous web and method of making is provided. The web comprises at least 50%, by weight of the fibrous web, of staple fibers and at least 10%, by weight of the fibrous web, of non-fibrous latex binder, wherein, the staple fibers are autogenously bonded to each other and are bonded to each other by the latex binder.

18 Claims, 6 Drawing Sheets

(56) References Cited

U.S. PATENT DOCUMENTS

| | | | | |
|---|---|---|---|---|
| 2003/0022581 A1* | 1/2003 | Tsai | ................ | A61F 13/15252 |
| | | | | 442/364 |
| 2004/0058607 A1 | 3/2004 | Bodaghi | | |
| 2005/0033252 A1* | 2/2005 | Schneider | ............ | A61F 13/537 |
| | | | | 604/367 |
| 2005/0118916 A1* | 6/2005 | Ducker | ............ | A61F 13/15203 |
| | | | | 442/385 |
| 2005/0266230 A1* | 12/2005 | Hill | ........................ | A47L 13/16 |
| | | | | 428/317.9 |
| 2006/0128247 A1* | 6/2006 | Skoog | .................... | D04H 1/407 |
| | | | | 442/384 |
| 2007/0135787 A1* | 6/2007 | Raidel | .............. | A61F 13/15707 |
| | | | | 604/383 |
| 2012/0121674 A1* | 5/2012 | Pedoja | .................... | A47L 13/17 |
| | | | | 424/401 |
| 2013/0101805 A1* | 4/2013 | Altshuler | ................ | B32B 5/022 |
| | | | | 428/172 |
| 2014/0163504 A1* | 6/2014 | Bianchi | ............ | A61F 13/53717 |
| | | | | 604/366 |

\* cited by examiner

CARDED NONWOVEN FIBROUS WEB AND USE IN ABSORBENT ARTICLES

CROSS REFERENCE TO RELATED APPLICATION

This application claims priority under 35 U.S.C. § 119 to European Patent Application Serial No. 16159074.0, filed on Mar. 8, 2016, the entire disclosure of which is hereby incorporated by reference.

FIELD OF THE INVENTION

The invention provides a carded nonwoven fibrous web formed of staple fibers which are autogenously bonded to each other and which are further consolidated with a latex binder. The fibrous web has superior caliper recovery after compression, high void volume and high in plane liquid permeability. Use of the fibrous web in absorbent articles for personal hygiene such as diapers, pants, or feminine hygiene sanitary napkins and especially use of the fibrous web as acquisition layer in such articles is also contemplated herein.

BACKGROUND OF THE INVENTION

Absorbent articles, such as diapers and pants, typically comprise an acquisition system which is provided between the absorbent core and the topsheet. Often, air-through bonded nonwovens or carded resin bonded nonwovens are used as material for such acquisition systems, However, air-through bonded nonwovens often lack sufficient recovery in caliper after they have undergone compression applied on the nonwoven during manufacturing and during storage of the material in roll-form or, if the material is incorporated into an absorbent article, during storage of the absorbent articles in packaging (where the articles are typically considerably compressed) or during use of the absorbent article exerted by the wearer. Carded nonwovens which are consolidated by use of a binder sometimes do not provide the desired degree of void volume and are therefore used in combination with additional layers of the acquisition system, such as a layer of intra-fiber cross-linked cellulose fibers.
Therefore, there is a need for improved nonwoven materials which overcome the drawback described above.

SUMMARY OF THE INVENTION

The invention relates to a carded nonwoven fibrous web comprising at least 50%, by weight of the fibrous web, of staple fibers and at least 10%, by weight of the fibrous web, of non-fibrous latex binder, wherein, the staple fibers are autogenously bonded to each other and are bonded to each other by the latex binder.

The invention also relates to a method of making such carded nonwoven fibrous web, wherein the method comprises the steps of:
  a. forming a layer of staple fibers;
  b. air-through bonding the staple fibers to autogenously bond the fibers to each other;
  c. applying a liquid latex binder onto the air-through bonded staple fibers, wherein the weight-ratio of staple fibers to binder is in the range of 90:10 to 65:35; and
  d. curing air-through bonded staple fibers with the binder applied thereon at elevated temperatures to cross-link the binder and obtain the carded nonwoven fibrous web.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which.

DETAILED DESCRIPTION OF THE INVENTION

Definition of Terms

Figure 1:
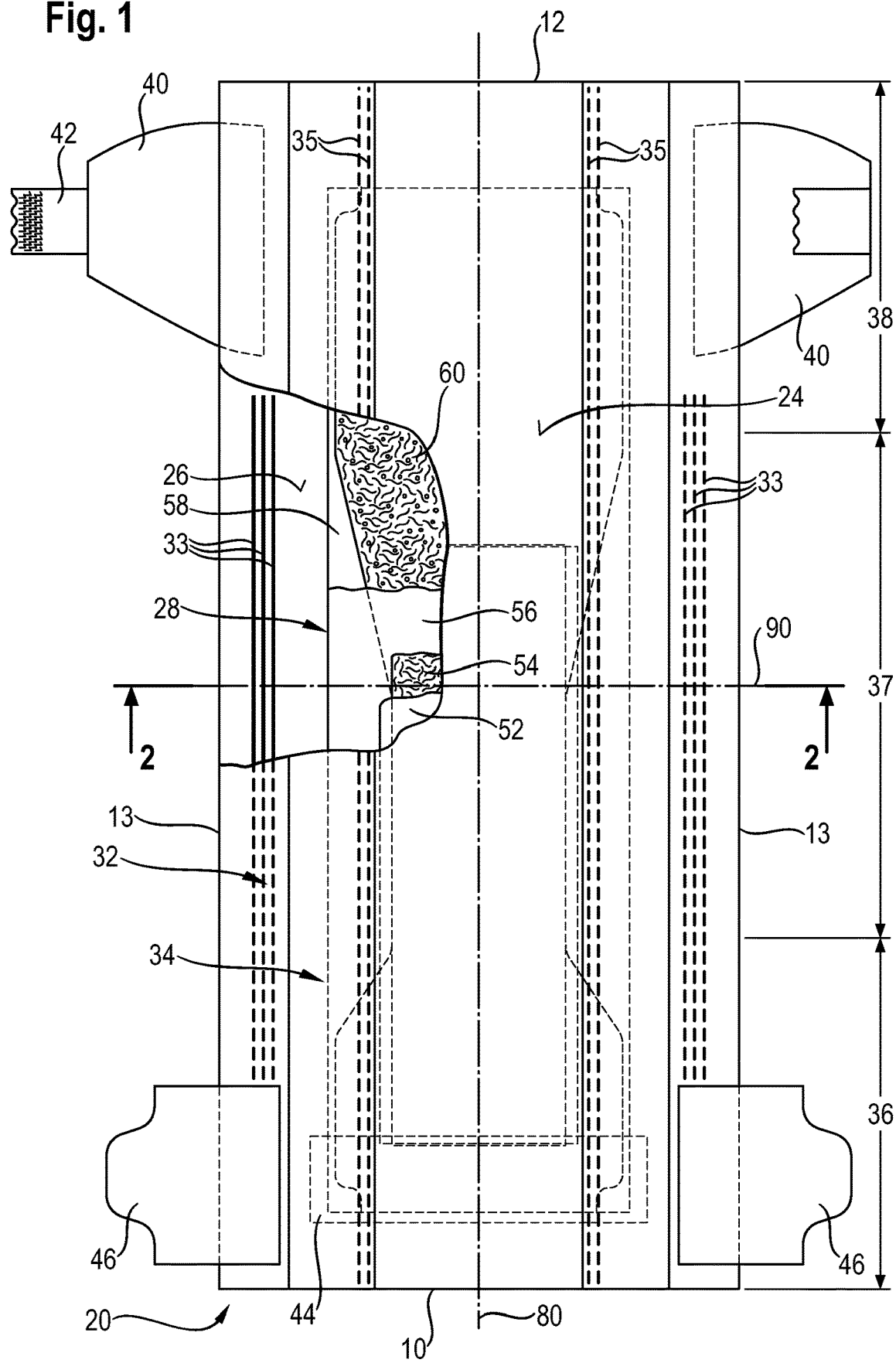
FIG. 1 is an absorbent article in the form of a diaper which may comprise the carded nonwoven fibrous web of the present invention

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants, inserts, feminine care absorbent articles such as sanitary napkins or pantiliners, and the like. As used herein, the term "exudates" includes, but is not limited to, urine, blood, vaginal discharges, sweat and fecal matter. Preferred absorbent articles of the present invention are disposable absorbent articles, more preferably disposable diapers and disposable pants.

The term "absorbent core" as used herein refers to a component, which is placed or is intended to be placed within an absorbent article and which comprises an absorbent material enclosed in a core wrap. The term "absorbent core" does not include an acquisition or distribution layer or any other component of an absorbent article which is not either an integral part of the core wrap or placed within the core wrap. The absorbent core is typically the component of an absorbent article which comprises all, or at least the majority of, superabsorbent polymer and has the highest absorbent capacity of all the components of the absorbent article.

As used herein, the terms "autogenously bonding", "autogenously bonded" and "autogenous bond" refer to bonding between discrete fibers of the carded nonwoven fibrous web using through-air bonding. Autogenous bonding does not apply solid contact pressure such as is applied for point-bonding or calendaring processes and is done independently of externally added additives which promote or facilitate bonding, such as adhesives, solvents, and the like.

As used herein, "bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core-and-sheath subsections, eccentric core/sheath subsections, side-by-side subsections, radial subsections, etc.

As used herein, the term "caliper" refers to the thickness of a web under a defined load, e.g. at 2.1.0 kPa, 4.0 kPa or 12.0 kPa.

As used herein, the term "cross-machine direction" (or CD) is the direction perpendicular to the machine direction.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

As used herein, the term "machine direction" (or MD) is the direction parallel to the flow of a material through a manufacturing line.

As used herein, "monocomponent" refers to fiber formed of a single polymer component or single blend of polymer components, as distinguished from Bicomponent or Multicomponent fiber.

As used herein. "multicomponent" refers to fiber having a cross-section comprising two or more discrete polymer components, two or more discrete blends of polymer components, or at least one discrete polymer component and at least one discrete blend of polymer components. "Multicomponent fiber" includes, but is not limited to, "bicomponent fiber."

As used herein, the term "non-consolidated fibers" refers to fibers which are not formed into a self-sustaining, integral web.

As used herein, a "nonwoven web" is a manufactured web of directionally or randomly oriented fibers, consolidated and bonded together. The term does not include fabrics which are woven, knitted, or stitch-bonded with yarns or filaments. The basis weight of nonwoven fabrics is usually expressed in grams per square meter ($g/m^2$).

As used herein, a "pantiliner" and a "sanitary napkin" generally have two end regions and a middle region (i.e. a crotch region). The pantiliner and the sanitary napkin has a body-facing surface and a garment facing surface. The size and shape of the absorbent structure positioned between the topsheet and the backsheet can be altered to meet absorbent capacity requirements, and to provide comfort to the wearer.

The garment facing surface of the pantiliner and of the sanitary napkin can have thereon pressure sensitive adhesive for affixing to a wearer's undergarments. Typically, such adhesive is covered with a release strip which is removed before affixing to the undergarment.

Pantiliners can also be provided with lateral extensions known commonly in the art as "flaps" or "wings" intended to extend over and cover the panty elastics in the crotch region of the user's undergarment. However, wings are normally not used with pantiliners but are more often used in sanitary napkins. Sanitary napkins and pantiliners of the present invention comprise barrier leg cuffs.

The term "substantially free of absorbent material" or "substantially absorbent material free" as used herein means that the basis weight of the absorbent material in the substantially absorbent material free areas is at least less than 10%, in particular less than 5%, or less than 2%, of the basis weight of the absorbent material in the rest of the absorbent core.

The term "superabsorbent polymers" (herein abbreviated as "SAP") as used herein refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP of the invention may in particular have a CRC value of more than 20 g/g, or more than 25 g/g, or from 20 to 50 g/g, or from 20 to 40 g/g, or 25 to 35 g/g. The SAP useful in the invention includes a variety of water-insoluble, but water-swellable polymers capable of absorbing large quantities of liquid bodily exudates.

The term "web" as used herein means a material capable of being wound into a roll. Webs may be nonwovens.

Carded Nonwoven Fibrous Web

The carded nonwoven fibrous web of the present invention comprises at least 50%, by weight of the carded nonwoven fibrous web, of staple fibers and at least 10%, by weight of the carded nonwoven fibrous web, of a latex binder. Staple fibers are short fibers, they may have a length of from 10 mm to 120 mm, or from 25 mm to 80 mm, or from 25 mm to 60 mm.

The fibers of the carded nonwoven fibrous web are staple fibers. The carded nonwoven fibrous web may essentially consist of staple fibers and a latex binder, i.e. the carded nonwoven fibrous web may, in addition to the staple fibers and latex binder, consist of minor amounts of additives, such as odor control additives, perfumes, colored pigments or the like.

For the present invention, staple fibers laid down by a carding process form a layer of non-consolidated fibers. The layer then undergoes a through-air bonding process to form an autogenously bonded web.

Thereafter, a latex binder is applied on the autogenously bonded carded nonwoven fibrous web and the fibrous web with the binder applied thereon undergoes a curing step to cross-link the binder.

The basis weight of the carded nonwoven fibrous web may be from 20 to 100 $g/m^2$, or from 30 to 80 $g/m^2$, or from 35 to 70 $g/m^2$.

Carding Process

Carding is a mechanical process using staple fibers. To obtain staple fibers, the fibers are first spun, cut to a few centimeters length, and put into bales (bundles of compressed fibers). The carding process starts with the opening of the bales of fibers which may be blended and are typically conveyed to the next stage by air transport. They are then combed into a web by a carding machine, such as a rotating drum or series of drums covered in fine wires or teeth. The precise configuration of cards will depend on the fabric weight and fiber orientation required. The web can be parallel-laid, where most of the fibers are laid in the direction of the web travel, or they can be random-laid. Typical parallel-laid carded webs result in good tensile strength, low elongation and low tear strength in the machine direction and the reverse in the cross direction.

In contrast to carded nonwoven webs, spunlaid and meltblown nonwoven webs are typically made in one continuous process. Fibers are spun and then directly dispersed into a web by deflectors or directed with air streams. The fibers of a spunlaid or meltblown nonwoven are considerably longer compared to staple fibers.

Through Air Bonding

As used herein, through-air bonding or "TAB" means a process of bonding staple fibers of the layer of non-consolidated fibers in which air is forced through the web, wherein the air is sufficiently hot to melt (or at least partly melt, or melt to a state where the fiber surface becomes sufficiently tacky) the polymer of a staple fiber or, if the staple fibers are multicomponent fibers, wherein the air is sufficiently hot to melt (or at least partly melt, or melt to a state where the fiber surface becomes sufficiently tacky) one of the polymers of which the fibers of the web are made. The air velocity is typically between 30 and 90 meter per minute and the dwell time may be as long as 6 seconds. The melting and resolidification of the polymer provides the bonding between different staple fibers.

Figure 3:
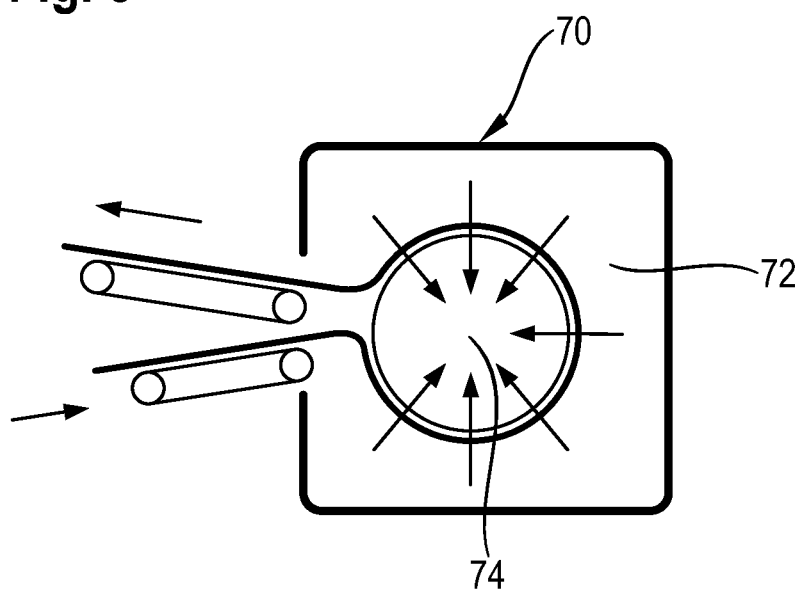
FIG. 3 is schematic representation of an air-though bonder

A through air bonder is schematically shown in FIG. 3. In the through-air bonder 70, air having a temperature above the melting temperature of the polymer of the staple fiber or, if the staple fibers are multicomponent fibers, above the melting temperature of a first fiber component and below the melting temperature of a second fiber component, is directed from the hood 72, through the web, and into the perforated roller 74. Alternatively, the through-air bonder may be a flat arrangement wherein the air is directed vertically downward onto the web. The operating conditions of the two configurations are similar, the primary difference being the geometry of the web during bonding.

The hot air melts the staple fiber, or, for multicomponent fibers, the lower melting polymer component and thereby forms bonds between the staple fibers to consolidate and integrate the layer of staple fibers into a web.

As an example for a bicomponent fiber, when polypropylene and polyethylene are used as polymer components A and B respectively, the air flowing through the through-air bonder usually has a temperature ranging from about 110° C. to about 162° C. at a velocity from about 30 to about 90 meters per minute. It should be understood, however, that the parameters of the through-air bonder depend on factors such as the type of polymers used and thickness of the fibrous layer.

Latex Binder

The carded nonwoven fibrous web of the present invention comprises at least 10%, by weight of the carded nonwoven fibrous web, of a latex binder. The carded nonwoven fibrous web of the present invention may comprise at least 15%, or at least 20%, or at least 25%, or at least 30%, by weight of the carded nonwoven fibrous web, of a latex binder. The carded nonwoven fibrous web of the present invention comprises less than 50%, by weight of the carded nonwoven fibrous web, of a latex binder, and may comprise less than 45%, or less than 40%, or less than 35%, by weight of the carded nonwoven fibrous web, of a latex binder.

A suitable latex binder is prepared by a process including the steps of:

(1) polymerizing a monomer mixture comprising styrene, itaconic acid, surfactant and water soluble free radical initiator to form a seed;

(2) sequentially adding equal increments of a monomer mixture of styrene, butadiene and acrylic acid to the seed under emulsion polymerization conditions to form a styrene-butadiene-acrylic acid copolymer; and then (3) neutralizing the styrene-butadiene-acrylic acid copolymer to a pH of about 4.5 to 7 to form the latex binder.

The binder is applied onto the autogenously bonded carded fibrous web. Subsequently, the latex binder is cured, using methods well known in the art, such as by application of heat or radiation. The term "cured" refers to the latex binder being cross-linked. The curing of the treated staple fibers is affected by a temperature above the glass transition temperature of the binder.

The latex binder may be prepared by well-known conventional emulsion polymerization techniques using one or more ethylenically unsaturated monomers and a polymeric surfactant as herein disclosed and additional conventional additives such as free-radical initiators, optional chain transfer agents, chelating agents and the like can be utilized as set forth in U.S. Pat. No. 5,166,259 to Schmeing and White.

In accordance with a preferred embodiment, the latex is prepared by polymerizing a monomer mixture comprising styrene, itaconic acid, surfactant and a water soluble free radical initiator to form a seed. A monomer mixture is then added incrementally to the seed under emulsion polymerization conditions. The monomer mixture includes styrene, butadiene, and acrylic acid. The acrylic acid can help in the cross-linking process of the binder upon curing. The monomer mixture is preferably added incrementally to the seed to form a styrene-butadiene-acrylic acid copolymer. In a preferred embodiment, the monomer mixture includes about 34-70 wt % styrene of the total composition. The monomer mixture also includes about 0.5-2.5 wt % itaconic acid, preferably 2 wt % itaconic acid of the total composition, about 20-55 wt % butadiene and acrylic acid in an amount of about 6-10 wt %, preferably 8 wt %.

A surfactant is added to the monomer mixture in an amount of about 0.05-2.0 wt %. The surfactant may be most any suitable emulsifier, soap, or the like well known in the art and suitable at the pH of the latex. Examples of suitable emulsifiers and surfactants include alkyl sulfates, alkyl sulfosuccinates, alkyl aryl sulfonates, alpha-olefin sulfonates, fatty or rosin acid salts, only or octyl phenol reaction products of ethylene oxide and the like. Other surfactants that may be used include those identified in Surface Active Agents, Schwartz and Berry, Vol. 1, Interscience Publishers, Inc., New York, 1958; Surface Activity, Moilet, Collie and Black, D. Van Nostrand Company, Inc., New York, 1961; Organic Chemistry, Feiser and Feiser, D.C. Heath and Company, Boston, 1944; and The Merck Index, Seventh Edition, Merck & Co., Inc., Rahway, N.J., 1960, all of which are hereby incorporated by reference.

The copolymer is then neutralized to a pH of about 4.5 to 7.0 to form the latex. The pH of the latex is neutralized by addition of a base. Examples of a suitable base include potassium hydroxide, sodium bicarbonate, ammonium hydroxide, sodium hydroxide and the like. The amount of base added to the latex is adjusted to obtain the desired pH range as is well known in the art.

Polymerization is typically carried out from about 65° C. to 75° C. Polymerization is generally conducted for about 4 to 24 hours, however polymerization conditions may vary as desired to provide different conversion levels of monomer to copolymer. The monomer mixture is allowed to react until substantially constant solids at which time at least 99% of the monomers have been converted.

The Staple Fibers

The carded nonwoven fibrous web of the present invention comprises at least 50%, by weight of the carded nonwoven fibrous web, of staple fibers. The carded nonwoven fibrous web of the present invention may comprise at least 55%, or at least 60%, or at least 65%, or at least 70%, by weight of the carded nonwoven fibrous web, of staple fibers. The carded nonwoven fibrous web of the present invention comprises less than 90%, by weight of the carded nonwoven fibrous web, of staple fibers, and may comprise less than 85%, or less than 80%, or less than 75%, by weight of the carded nonwoven fibrous web, of staple fibers.

The fibers useful for the carded nonwoven fibrous web of the present invention are monocomponent fibers as well as multicomponent fibers. Multicomponent fibers are especially useful. Suitable multicomponent fibers are bicomponent fibers, such as core/sheath bicomponent fibers and side-by-side bicomponent fibers. The core/sheath bicomponent fibers may be concentric or eccentric fibers.

The monocomponent or multicomponent fibers may be made of polymeric materials, such as polyolefins (e.g. polypropylene, or polyethylene), polyester, polyethylene terephthalate (PET), CoPET, polybutylene terephthalate, polyamide, polylactic acid, viscose, and combinations thereof. The polymers may also comprise copolymers such as Co-PET. If the staple fibers comprise core/sheath bicomponent fibers, it is desirable that the sheath is made of a polymer which has a melting point below the melting point of the polymer which forms the sheath. If such bicomponent fibers are subjected to through-air bonding, the temperature of the through air bonding process is selected such that the polymer of the sheath is at least partially transferred to a molten state (or partly molten state, or molten to a state where the fiber surface becomes sufficiently tacky) such that the fibers bond together while the core of the bicomponent fiber remains substantially unaffected.

If side-by-side bicomponent fibers are used, the polymers forming the first and second component may also have different melting points. If such bicomponent fibers are subjected to through-air bonding, the temperature of the through air bonding process is selected such that the polymer of the component having the lower melting point is molten is at least partially transferred to a molten state (or to a state where the fiber surface becomes sufficiently tacky) such that the fibers bond together while the polymer of the component having the higher melting point remains substantially unaffected.

The carded nonwoven fibrous web may comprise a mixture of different types of fibers, such as a mixture of monocomponent fibers and bicomponent fibers. The staple fibers of the carded nonwoven fibrous web may comprise at least 20%, or at least 35%, or at least 50%, or at least 60%, or at least 70%, or at least 80%, by total weight of the staple fibers, of multicomponent fibers, such as core/sheath or side-by-side bicomponent fibers. The staple fibers may also consist only of multicomponent fibers, such as bicomponent fibers. The staple fibers may be a mixture of different multicomponent fibers, e.g. a mixture of different bicomponent fibers.

The carded nonwoven fibrous web may also comprise monocomponent fibers. For example, the staple fibers may comprise at least 5%, or at least 10%, or at least 15%, or at least 20%, or at least 25%, by total weight of the staple fibers, of monocomponent fibers. The carded nonwoven fibrous web may not comprise more than 50%, or not more than 40%, or not more than 30%, by total weight of the staple fibers, of monocomponent fibers.

The staple fibers of the carded nonwoven fibrous web may consist of a mixture bicomponent fibers (such as core/sheath bicomponent fibers or side-by-side bicomponent fibers) and monocomponent fibers, such that the bicomponent fibers and the monocomponent fibers together form 100% of the total weight of the staple fibers.

The shape of the staple fibers of the carded nonwoven fibrous web may be round (i.e. fibers having a circular cross-section). Alternatively, the staple fibers may have non-round shape, such as multilobal fibers (e.g. trilobal fibers), flat fibers ("ribbon-like" cross-section), rhomboid fibers, or triangular fibers. In multilobal fibers, a central section is encircled by a multiplicity of lobes. E.g. in a trilobal fiber, the central section is encircled by three lobes.

The staple fibers may comprise or consist of a mixture of solid, round bicomponent fibers (such as core/sheath or side-by-side bicomponent fibers) and solid, multilobal (such as trilobal) monocomponent fibers. Alternatively, the staple fibers may comprise or consist of a mixture of solid, round bicomponent fibers (such as core/sheath or side-by-side bicomponent fibers) and solid, round monocomponent fibers.

Overall, for the carded nonwoven fibrous web of the present invention, which has been subjected to through air bonding prior to application of the latex binder, the latex binder has been found to distribute more evenly over the fiber surfaces throughout the carded nonwoven fibrous web and shows a reduced tendency to "collect" in clusters at the cross-points of the staple fibers compared to resin-bonded carded webs without autogenous bonds.

At least 50%, or at least 60%, or at least 65%, or at least 70%, or at least 75% of the total weight of the staple fibers may have a first diameter (=first type of fibers). The first type of fibers may constitute all of the fibers of the carded nonwoven fibrous web, or may constitute not more than 95%, or not more than 90%, or not more than 85% of the total weight of the staple fibers. The staple fibers of the carded nonwoven fibrous web may further comprise at least 5%, or at least 10%, or at least 15%, or at least 20%, or at least 25% of the total weight of the staple fibers, fibers having a second diameter fiber (=second type of fibers), which is smaller than the diameter of the first type of. The second type of fibers may constitute not more than 35%, or not more than 30%, or not more than 25% of the total weight of the staple fibers. The first and second type of fibers together may constitute 90%, or 95%, or 100% of the total weight of the staple fibers of the carded nonwoven fibrous web.

The diameter of the first type of fibers may be at least 50% larger, or at least 60% larger, or at least 80% larger, or at least 100%, or at least 200% larger than the diameter of the first type of fibers. The diameter of the first type of fibers may be from 3 to 10 denier, or from 4 to 8 denier. The diameter of the second type of fibers may be from 0.8 denier to 2.5 denier, or from 1.0 denier to 2.0 denier.

Having a relatively high percentage of fibers with relatively high fiber diameter (e.g. from 3 to 10 denier) provides carded nonwoven fibrous webs with a relatively high degree of porosity. Such high degree of porosity is especially desirable for use of the material as acquisition material in an absorbent article.

Compared with the through air bonding applied for the carded nonwoven fibrous web of the present invention, the use of spunlace material, in which a carded fibrous layer is subjected to hydroentagling to consolidate the web and impart integrity, typically requires fibers with a relatively low fiber diameter. The low fiber diameter is needed as the fibers need to be able to bend sufficiently in order to entangle the fibers with each other. However, making carded nonwoven fibrous webs made of low denier fibers generally leads to webs with relatively low porosity, which makes them less attractive for use as acquisition material in absorbent articles.

Moreover, the through air bonding provides for autogenous bond sites which are relatively stable versus hydro-engangled webs with no fiber to fiber bonds. During the application of latex binder and subsequent curing, the web is typically strained as it travels e.g. between calendar rolls. In the absence of stable fiber to fiber bonds (i.e. the autogenous bond sites), the fibers tend to rearrange and the web often loses a considerable portion of its initial loftiness, leading to a flatter web with reduced void volume. Hence, the combination of autogenous fiber to fiber bonds with the application of a latex binder has been found to be especially advantageous for webs to be used as acquisition layer in absorbent articles.

Having a certain amount of staple fibers with rather small fiber diameter helps to increase overall opacity of the web, especially if shaped fibers, such as multilobal (e.g. trilobal) fibers are applied, given that non-round fibers have a higher ratio of fiber surface area to fiber volume. Increased opacity is desirable as it helps to disguise body exudates beneath the acquisition layer (towards the backsheet). While fibers with a rather small fiber diameter can increase opacity of the web, it has been found that they do not negatively impact the resiliency (i.e. improved caliper recovery upon compression).

The Carded Nonwoven Fibrous Web with Autogenous Bonds and Latex Binder

It has been found that compared to carded nonwoven fibrous webs which have solely undergone through-air bonding to consolidate the staple fibers into a coherent web, the additional, subsequent application of a latex binder facilitates nonwoven fibrous webs with improved caliper recovery after compression at different pressure levels.

For example (see Examples below), upon compression at 12 kPa, the carded nonowoven fibrous webs of the present invention show a caliper improve in compression recovery of at least 5% or at least 7%, compared to a carded, through-air bonded nonwoven fibrous web without additional latex bonding. A pressure of up to 12 kPa may occur for highly compressed absorbent articles in packages.

Typical use conditions of absorbent articles may subject the article to pressures of about 1 kPa or up to 4 kPa upon pressure exerted by the wearer. Upon such pressures, it has been found that the carded nonowoven fibrous webs of the present invention show a caliper improvement in compression recovery (upon compression at 4 kPa) of at least 5% or at least 7%; or, upon compression at 1 kPa, of at least 4% compared to a carded, through-air bonded nonwoven fibrous web without additional latex bonding.

Moreover, air permeability of carded nonwoven webs with autogenous bonds and latex binder has shown to increase (for webs which have not undergone compression) by at least 4%, or by at least 10%, or by at least about 20%, or by at least about 30% compared to a carded, through-air bonded nonwoven fibrous web without additional latex bonding (see Examples below).

Also, permeability, measured by In Plane Radial Permeability (IPRP) has been found to increase (for webs which have not undergone compression) by at least 10%, or at least 20%, or at least 25% compared to a carded, through-air bonded nonwoven fibrous web without additional latex bonding (see Examples below).

Moreover, it has been found that IPRP is not only improved for the carded nonwoven fibrous web which has not undergone compression but is also improved for carded nonwoven fibrous webs which have been previously compressed, compared to a carded, through-air bonded nonwoven fibrous web without additional latex bonding (see Examples below).

Permeability, measured by In Plane Radial Permeability (IPRP) has been found to increase (for webs 24 h after compression at 4 kPa) by at least 10%, or at least 20%, or at least 25% compared to a carded, through-air bonded nonwoven fibrous web without additional latex bonding (see Examples below).

Hence, the carded nonwoven fibrous webs of the present invention have been found to have improved properties versus known carded fibrous webs without latex binder, especially with regard to properties important for use as acquisition layers of such fibrous webs in absorbent articles.

Compared to known carded nonwoven fibrous webs which have only been consolidated by use of a latex binder without having also undergone through-air bonding to form autogenous bonds between staple fibers, the fibrous web of the present invention may have good void volume: Upon curing the nonwoven webs to cross-link the binder, the nonwovens are typically subjected to tension, e.g. as they travel between a pair of rolls (to stabilize their position along the manufacturing line). If the staple fibers have not been bonded to each other to form a coherent web prior to this process, the staple fibers tend to re-arrange their position within the fibrous layer, which may reduces loft and thus, void volume of the subsequently obtained web.

Further to providing improved void volume, such carded nonwoven fibrous webs having autogenous fiber bonds in addition to being consolidated with a latex binder, may have improved softness due to their improved loftiness, when compared to a carded nonwoven fibrous web with no autogenous bonds.

Furthermore, upon being subjected to tension in MD in the manufacturing process, the re-arrangement of the non-consolidated staple fibers can result in a relatively high degree of fiber orientation in MD. Typically, fiber orientation of the staple fibers in carded nonwoven fibrous webs with only latex bonding is in the range of 5/1 (MD/CD) up to 10/1 (MD/CD). This relatively high degree of fiber orientation results in relatively high tensile strength of the web in MD compared to the tensile strength in CD. When such webs are incorporated into absorbent articles, they often show a relatively high tendency to necking when subjected to MD tension (i.e. they become narrower in CD). This necking can pose problems in the manufacturing process, e.g. when adhesive needs to be applied along the side edges of the web to attach the endless web onto other layers of the absorbent article.

By subjecting the non-consolidated staple fibers to through-air bonding prior to application of the latex binder, the nonwoven non-consolidated staple fibers can be transformed into a self-sustaining web relatively quickly and before the web undergoes strain in the curing process step to cross-link the binder. Due to the autogenous bonds between the staple fibers, subsequent fiber re-arrangement can be reduced and hence, the carded nonwoven fibrous webs of the present invention can be facilitated with less fiber orientation in MD (i.e. with more randomly arranged fibers).

Method of Making

The method of making the carded nonwoven fibrous web of the present invention comprises the steps of:

In a first step, a layer of staple fibers is formed. Staple fibers are formed by a carding process and laid down on a conveyor belt or drum to form a layer of non-consolidated staple fibers. The layer is preferably laid down in form of a continuous layer. The layer of non-consolidated fibers may be a homogeneous layer having substantially homogeneous basis weight. "Substantially homogeneous basis weight" is to be understood, in the sense that the basis weight may vary slightly due to process conditions, especially for relatively low basis weight fiber lay down; however, the basis weight is not varied intentionally throughout the layer of non-consolidated staple fibers. Alternatively, the basis weight may vary across CD and/or MD, i.e. the basis weight differs intentionally in CD and/or MD.

In a subsequent method step, the layer of non-consolidated staple fibers is subjected to air-through bonding. Air through bonders are described in more detail above. Due to the air-through bonding, the staple fibers are autogenously bonded to each other. As a result of the air-through bonding, a consolidated nonwoven fibrous web with relatively high loft is formed.

Thereafter, a liquid latex binder is applied onto the consolidated nonwoven fibrous web. The latex binder is preferably applied homogeneously onto one of the two surfaces of the fibrous web. The ratio of staple fibers to latex binder is from 90/10 to 60/40 (by weight of the staple fibers and binder). The ratio of staple fibers to latex binder may be from 90/10, or from 85/15, or from 80/20 or from 75/25, up to 60/40, or up to 65/45, or up to 70/30. The binder may be applied by known methods, such as by directing the consolidated nonwoven fibrous web through a bath or basin, which contains the liquid latex binder (also referred to as "kiss roll application", by spraying the liquid latex binder onto the consolidated nonwoven fibrous web, or by foam application, whereby the liquid latex binder is in a foamed state, with which the fibrous web is impregnated.

Then, the web with the binder applied thereon is cured at an elevated temperature sufficient to cross-link the binder (however, not as high as to melt the staple fibers) to obtain the carded nonwoven fibrous web of the present invention.

Alternatively, though less desirable, it is also possible to apply the liquid latex binder onto a layer of non-consolidated staple fibers which have not previously undergone air-through bonding. The layer of non-consolidated fibers with the latex binder applied thereon is then subjected to air-through bonding to autogenously bond the fibers to each other and subsequently to a curing step at an elevated temperature sufficient to cross-link the binder (however, not as high as to melt the staple fibers) to obtain the carded nonwoven fibrous web of the present invention.

In still another alternative, though less desirable, the liquid latex binder is applied onto a layer of non-consolidated staple fibers which have not previously undergone air-through bonding. The layer of non-consolidated fibers with the latex binder applied thereon is then subjected to a curing step at an elevated temperature sufficient to cross-link the binder (however, not as high as to melt the staple fibers) to obtain the carded nonwoven fibrous web of the present invention, and, subsequently, to air-through bonding to autogenously bond the fibers to each other.

Generally, the process has to be done such as to consider the melting point of the fibers (or the sheath of the fibers, if bicomponent fibers are used) and the curing temperature of the latex binder.

It may also be possible, though less desirable, to cure the latex binder and autogenously bond the staple fibers to each other in one process step if the melting point of the fibers (or the sheath of fibers, if bicomponent fibers are used) and the curing temperature of the latex binder are in the same range. Notably, this is different from the known curing of latex binders applied on nonwoven webs, which do not use temperatures at which the fibers would melt and bond to each other.

The web may be wound up in roll form for storage or transport. Alternatively, the web may be directly conveyed to a subsequent method step, such as a step whereby the web is incorporated into an absorbent article.

Absorbent Articles

Figure 2:
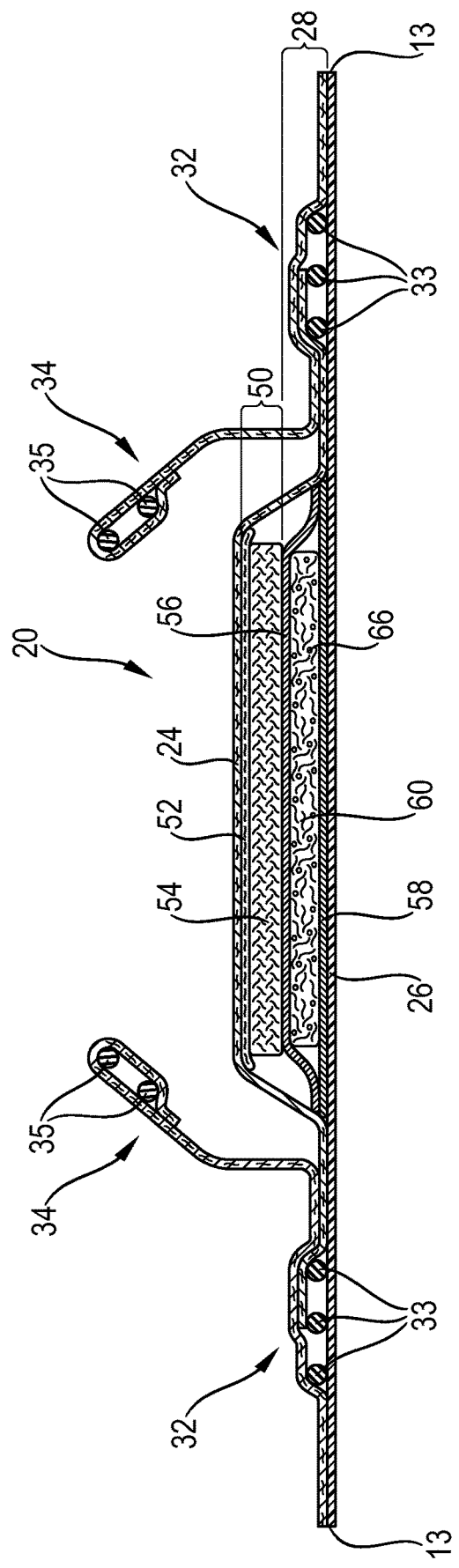
FIG. 2 is a transversal cross-section of the diaper of FIG. 1.

Referring to FIGS. 1 and 2, an example absorbent article 20 is described. FIG. 1 is top plan view of the absorbent articles 20 (shown here: a diaper), in a flat-out state, with portions of the structure being cut-away to more clearly show the construction of the absorbent articles 20. These absorbent articles 20 are shown for illustrative purposes only as the present disclosure may be used for making a wide variety of diapers or other absorbent articles.

The absorbent article 20 comprises a liquid permeable topsheet 24, a liquid impermeable backsheet 26, an absorbent core 28 positioned intermediate the topsheet 24 and the backsheet 26, an optional acquisition layer 52 underneath the topsheet, and, optionally, a distribution layer 54 beneath the acquisition layer and above the absorbent core. The absorbent article 20 comprises a front waist edge 10 (in a pantiliner or sanitary napkin, this edge of the article would be referred to as a front edge instead of front waist edge, given the article is considerably smaller and not worn around the waist of the wearer), and a back waist edge 12 (in a pantiliner or sanitary napkin, this edge of the article would be referred to as a back edge instead of back waist edge, given the article is considerably smaller and not worn around the waist of the wearer), and two longitudinal side edges 13. The front waist edge 10 is the edge of the absorbent article 20 which is intended to be placed towards the front of the user when worn, and the rear waist edge 12 is the opposite edge. The absorbent article 20 has a longitudinal dimension and a lateral dimension and may be notionally divided by a longitudinal axis 80 extending from the front waist edge 10 to the back waist edge 12 of the absorbent article 20 and dividing the absorbent article 20 in two substantially symmetrical halves relative to the longitudinal axis, when viewing the absorbent article 20 from the wearer-facing side in a flat, laid out configuration, as e.g. illustrated in FIG. 1.

The absorbent article 20 may be divided by a lateral axis 90 into a front half and a back half of equal length measured along the longitudinal axis 80, when the absorbent article 20 is in a flat, laid-out state. The absorbent article's lateral axis 90 is perpendicular to the longitudinal axis 80 and is placed at half the longitudinal length of the absorbent article 20.

The longitudinal dimension of the absorbent article extends substantially parallel to the longitudinal axis 80 and the lateral dimension extends substantially parallel to the lateral axis 90.

The absorbent article 20 may be notionally divided into a front region 36, a back region 38 and a crotch region 37 located between the front region 36 and the back region 38 of the absorbent article 20. Each of the front, back and crotch regions are ⅓ of the longitudinal dimension of the absorbent article 20.

The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers. In the examples below, the ADS 50 comprises two layers: a distribution layer 54 and an acquisition layer 52 disposed between the absorbent core and the topsheet.

The ADS may be free of superabsorbent polymer.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 $g/m^2$ to 400 $g/m^2$, in particular from 80 $2/m^2$ to 300 $g/m^2$.

The distribution layer may for example comprise intra-fiber cross-linked cellulose fibers. The intra-fiber cross-linked cellulosic fibers may be crimped, twisted, or curled, or a combination thereof including crimped, twisted, and curled. The intra-fiber cross-linked cellulosic fibers provide higher resilience and therefore higher resistance to the first absorbent layer against the compression in the product packaging or in use conditions, e.g. under the weight of a wearer. This provides a relatively high void volume, permeability and liquid absorption, and hence reduced leakage and improved dryness.

The distribution layer comprising intra-fiber cross-linked cellulose fibers, may comprise other fibers, but this layer may advantageously comprise at least 50%, or 60%, or 70%, or 80%, or 90% or even up to 100%, by weight of the layer, of intra-fiber cross-linked cellulose fibers. Examples of such mixed layers of intra-fiber cross-linked cellulose fibers with other fibers may comprise 60% to 80%, or 60% to 75% by weight of intra-fiber cross-linked cellulose fibers, 5% to 20%, or 5% to 15% by weight of polyester (PET) fibers, and 5% to 20%, or 5% to 15% by weight of untreated pulp fibers. In another example, the distribution layer may comprise 65% to 80% by weight of intra-fiber cross-linked cellulose fibers, 10% to 20% by weight of lyocell fibers, and 5% to 15% by weight of PET fibers. In another example, the distribution layer may comprise 68% by weight of intra-fiber cross-linked cellulose fibers, 16% by weight untreated pulp fibers, and 16% by weight PET fibers.

The absorbent article 20 may further comprise an acquisition layer 52, which is provided directly beneath the topsheet and above the absorbent core and, if present, above the distribution layer). The function of the acquisition layer 52 is to quickly acquire the fluid away from the topsheet so as to provide a good dryness for the wearer. The acquisition layer may typically be or comprise a non-woven material, for example a SMS or SMMS material, comprising a spun-bonded, a melt-blown and a further spunbonded layer or alternatively a carded chemical-bonded nonwoven. The nonwoven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex. However, in a preferred absorbent article of the present invention, the acquisition layer comprises or consists of the carded nonwoven fibrous web of the present invention. The acquisition layer may comprise or consist of one carded nonwoven fibrous web of the present invention or may comprise or consist of two or more (e.g. two, three or four) of the carded nonwoven fibrous webs of the present invention.

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

The absorbent core 28 may comprise an absorbent material 60 that is a blend of cellulosic fibers (so called "airfelt") and superabsorbent polymers in particulate form encapsulated in one or more webs, see for example U.S. Pat. No. 5,151,092 to Buell. Alternatively, the absorbent core 28 may be free of airfelt, or substantially free of airfelt, as described in further detail herein.

FIG. 1 also shows other typical diaper components such as a fastening system comprising fastening tabs 42 attached towards the back waist edge 12 of the absorbent article 20 and cooperating with a landing zone 44 towards the front waist edge 10 of the absorbent article 20. The absorbent article 20 may also comprise front ears 46 and back ears 40 as it is known in the art.

The absorbent article may comprise further optional other features such as leg cuffs 32 and/or barrier cuffs 34, front and/or back waist features such as front and/or elastic waistbands attached adjacent to the respective front and/or back waist edge of the absorbent article.

The topsheet 24, the backsheet 26, and the absorbent core 28 may be assembled in a variety of well known configurations, in particular by gluing or heat embossing. Exemplary diaper configurations are described generally in U.S. Pat. Nos. 3,860,003; 5,221,274; 5,554,145; 5,569,234; 5,580,411; and 6,004,306.

The diaper 20 may comprise leg cuffs 32 which provide improved containment of liquids and other body exudates. Leg cuffs 32 may also be referred to as leg bands, side flaps, barrier cuffs, or elastic cuffs. Usually each leg cuffs will comprise one or more elastic string 33, represented in exaggerated form on FIGS. 1 and 2, comprised in the diaper for example between the topsheet and backsheet in the area of the leg openings to provide an effective seal while the diaper is in use. It is also usual for the leg cuffs to comprise "stand-up" elasticized flaps (barrier leg cuffs 34) which improve the containment of the leg regions. The barrier leg cuffs 34 will usually also comprise one or more elastic strings 35, represented in exaggerated form in FIGS. 1 and 2.

"Airfelt-Free" Absorbent Core 28

The absorbent core 28 of the invention may comprise an absorbent material 60 enclosed within a core wrap 56 and 58. The absorbent material 60 may comprise from 80% to 100% of superabsorbent polymer (SAP) 66, such as SAP particles, by total weight of the absorbent material 60. The core wrap 160 is not considered as an absorbent material 60 for the purpose of assessing the percentage of SAP in the absorbent core 28.

By "absorbent material" it is meant a material which has absorbency and/or liquid retaining properties, such as SAP, cellulosic fibers as well as some hydrophilically treated synthetic fibers. Typically, adhesives used in making absorbent cores have no absorbency properties and are not considered as absorbent material. The SAP content may be substantially higher than 80%, for example at least 85%, at least 90%, at least 95% and even up to and including 100% of the weight of the absorbent material 60 contained within the core wrap 160. This above SAP content substantially higher than 80% SAP may provide a relatively thin absorbent core 28 compared to conventional absorbent cores typically comprising between 40-60% SAP and 40-60% of cellulosic fibers. The absorbent material 60 of the invention may in particular comprise less than 10% weight percent, or less than 5% weight percent, or even be substantially free of natural and/or synthetic fibers. The absorbent material 60 may advantageously comprise little or no cellulosic fibers, in particular the absorbent core 28 may comprise less than 15%, 10%, or 5% (airfelt) cellulosic fibers by weight of the absorbent core 28, or even be substantially free of cellulose fibers. Such absorbent core 28 may be relatively thin and thinner than conventional airfelt cores. FIG. 1, FIG. 2 and FIG. 3 are illustrations of an absorbent article 20 comprising an "airfelt-free" absorbent core 28.

"Airfelt-free" absorbent cores 28 comprising relatively high amount of SAP with various absorbent core designs have been proposed in the past, see for example in U.S. Pat. No. 5,599,335 (Goldman), EP1447066A1 (Busam), WO95/11652 (Tanzer), US2008/0312622A1 (Hundorf), and WO2012/052172 (Van Malderen).

The absorbent core 28 of the invention may comprise adhesive for example to help immobilizing the SAP 66 within the core wrap 56 and 58 and/or to ensure integrity of the core wrap, in particular when the core wrap is made of one or more substrates. The core wrap will typically extend over a larger area than strictly needed for containing the absorbent material 60 within.

The absorbent material 60 may be encapsulated in one or more substrates. The core wrap comprises a top side 56 facing the topsheet 24 and a bottom side 58 facing the backsheet 26, as shown in FIG. 2. The core wrap may be made of a single substrate folded around the absorbent material 60. The core wrap may be made of two substrates (one mainly providing the top side and the other mainly providing the bottom side) which are attached to another. Typical configurations are the so-called C-wrap and/or sandwich wrap. In a C-wrap, the longitudinal and/or transversal edges of one of the substrate are folded over the other substrate to form flaps. These flaps are then bonded to the external surface of the other substrate, typically by bonding with an adhesive. The so called C-wrap construction can provide benefits such as improved resistance to bursting in a wet loaded state compared to a sandwich seal.

The core wrap may be formed by any materials suitable for receiving and containing the absorbent material 60. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as polyethylene (PE), polyethylene terephthalate (PET) and in particular polypropylene (PP).

Test Methods

Unless indicated otherwise, all tests described herein are made with samples conditioned at least 24 hours at 23° C.+/−2° C. and 50%+/−10% Relative Humidity (RH).

Caliper Method

The caliper of the material sample is measured using a dial gauge or digital equivalent with a resolution of ±10 μm and a circular "foot" having a flat bottom circular surface with a diameter of 56 mm. The gauge is mounted over a base having a horizontal flat rigid upper surface, such that the entire bottom surface of the foot contacts the upper surface of the base.

The downward force exerted by the foot on the base or on a material sample inserted between the foot and the base is depending on the weight of the foot, i.e. depending on the exact equipment used.

The weight exerted by the foot of the gauge can be measured by mounting the gauge over a suitable top-loading balance such that the balance pan is in the same relative position to the gauge as the base. It is independent of the caliper of the material sample. The force is adjusted by adding weight to the foot such that the total weight is 518 g, i.e. the pressure exerted by the foot of 56 mm diameter is 2065±10 Pa.

The gauge is calibrated according to the manufacturer's instructions.

The material sample is cut as a circle of 6 cm diameter. Such material sample is placed on the base such that the foot is completely in contact with the material sample.

The caliper of the material sample is determined by reading the gauge with the foot resting on the base (G0). The foot of the gauge is then raised and the material is laid flat on the base. The foot is lowered gently onto the material sample and the gauge reading is taken 5 seconds after the foot comes into contact with the sample (GT). The caliper of the material sample at that location is the difference between the two readings (GT-G0). The caliper is the average of three replicates and is reported in millimeters rounded to the nearest 0.01 mm.

Compression at 1 kPa, 4 kPa and 12 kPa and Calculation of Caliper Recovery

Samples having size of 8×8 cm are cut from the carded nonwoven fibrous web. 10 samples are laid down on top of each other in a face to face relationship. A circular weight of 290 g and having a diameter of 6 cm, exerting a pressure of 1 kPa, is then placed on top of the pile of 10 samples and is left on the pile for 15 hours at 40° C. and 75% relative humidity (RH).

The caliper of each of the 10 sample is measured separately prior to putting the weight on the samples, immediately after the weight is removed and 24 hours after the weight is removed. During the 24 hours after the weight is removed, the samples are stored at 22° C. and 50% RH. The average of the 10 caliper measurements, respectively taken prior to applying the weight, immediately after removing the weight and 24 hours after removing the weight, is taken to report caliper.

The same procedure is followed for compression at 4 kPa and at 12 kPa, however, for compression at 4 kPa a circular weight of 1150 k and having a diameter of 6 cm is used, and for compression at 12 kPa a circular weight of 3460 g and having a diameter of 6 cm is used.

Caliper recovery [%] is calculated as:

$$\frac{\text{Caliper 24 h after weight is removed} \times 100}{\text{Caliper before compentsation}}$$

In Plane Radial Permeability (IPRP) Method

In plane radial permeability or IPRP or shortened to permeability in the present invention is a measure of the permeability of the nonwoven fabric and relates to the pressure required to transport liquids through the material. The following test is suitable for measurement of the In-Plane Radial Permeability (IPRP) of a porous material. The quantity of a saline solution (0.9% NaCl) flowing radially through an annular sample of the material under constant pressure is measured as a function of time. (Reference: J. D. Lindsay, "The anisotropic Permeability of Paper" TAPPI Journal, (May 1990, pp. 223) Darcy's law and steady-state flow methods are used for determining in-plane saline flow conductivity).

Figure 4:
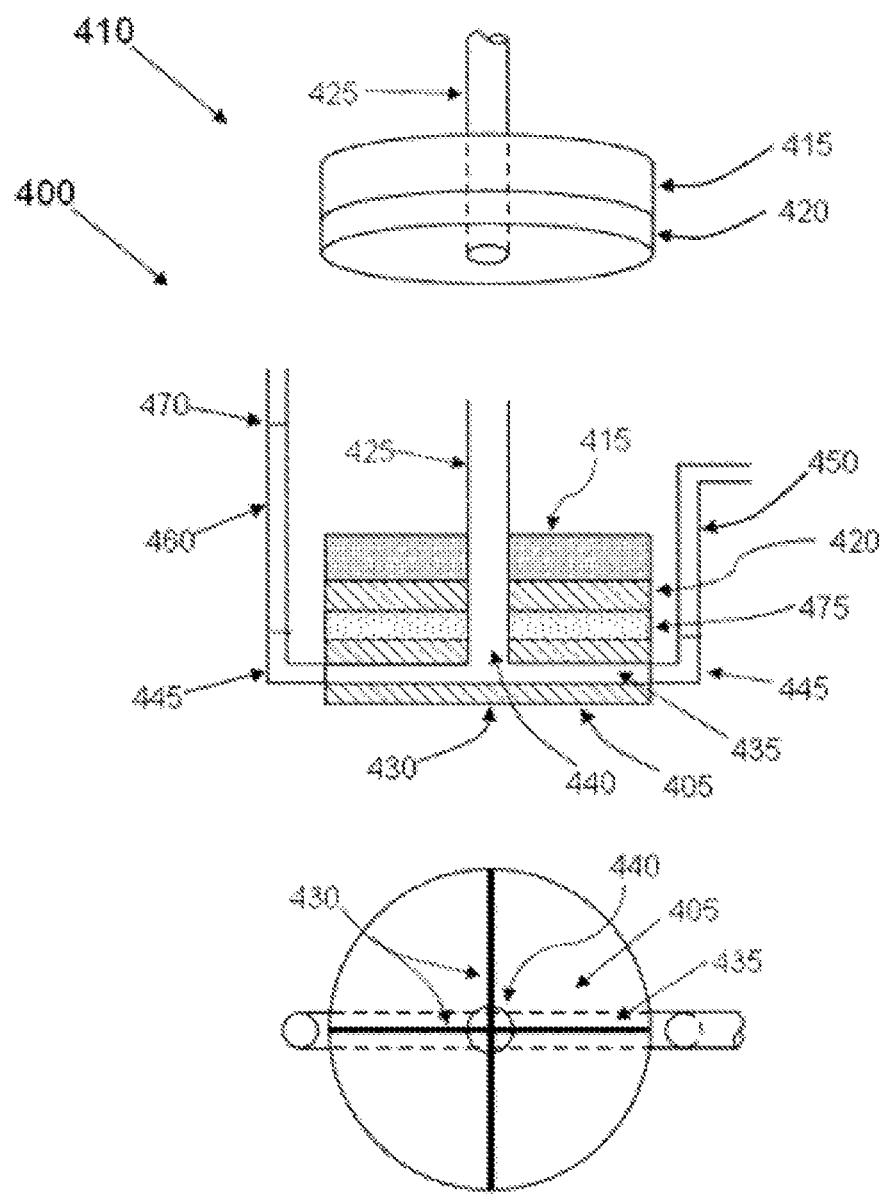
FIG. 4 is a schematic representation of an in plane radial permeability apparatus set up.
Figure 5:
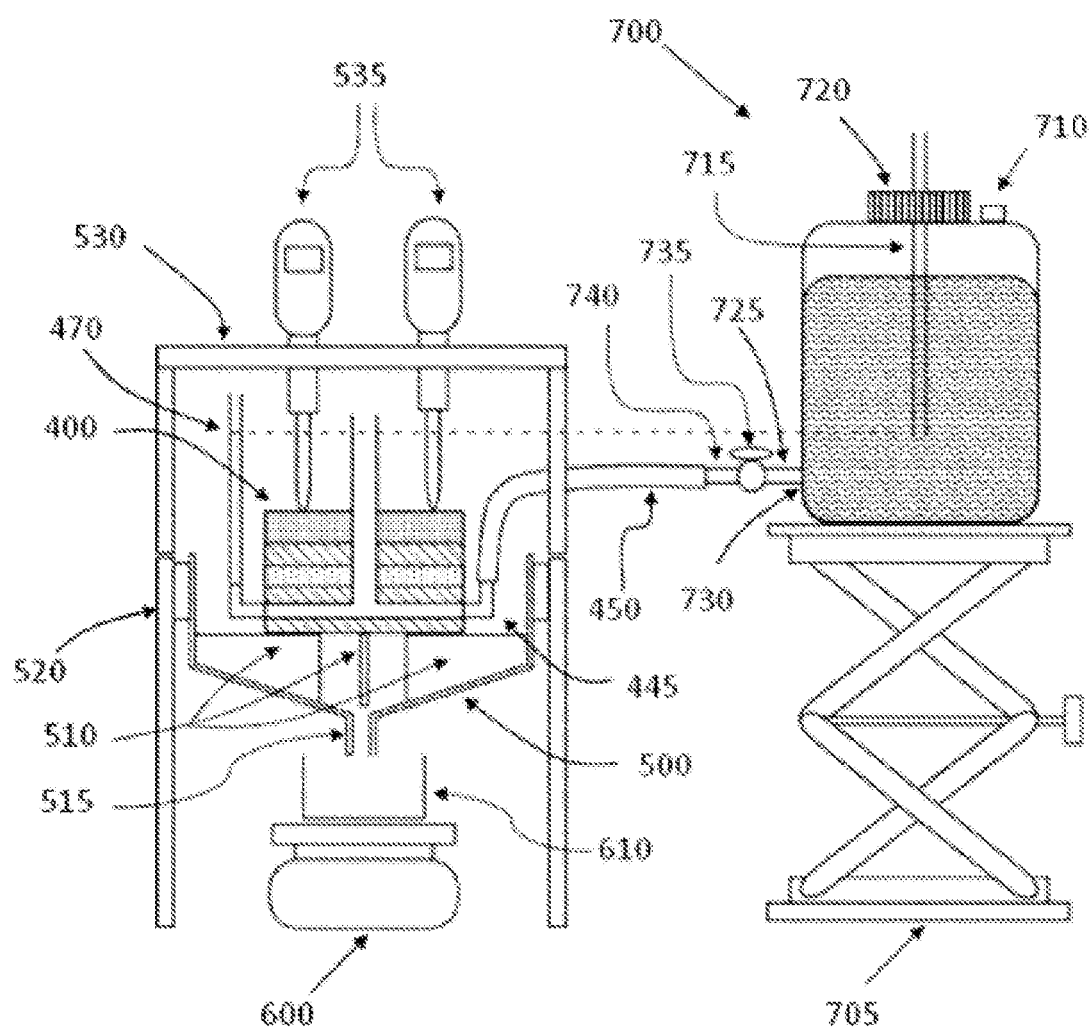
FIG. 5 is an alternate view of a portion of the in plane radial permeability apparatus set up shown in FIG. 4.

The IPRP sample holder 400 is shown in FIG. 4 and comprises a cylindrical bottom plate 405, top plate 420, and cylindrical stainless steel weight 415 shown in detail in FIG. 5.

Top plate 420 is 10 mm thick with an outer diameter of 70.0 mm and connected to a tube 425 of 190 mm length fixed at the center thereof. The tube 425 has in outer diameter of 15.8 mm and an inner diameter of 12.0 mm. The tube is adhesively fixed into a circular 12 mm hole in the center of the top plate 420 such that the lower edge of the tube is flush with the lower surface of the top plate, as depicted in FIG. 5. The bottom plate 405 and top plate 420 are fabricated from Lexan® or equivalent. The stainless steel weight 415 has an outer diameter of 70 mm and an inner diameter of 15.9 mm so that the weight is a close sliding fit on tube 425. The thickness of the stainless steel weight 415 is approximately 25 mm and is adjusted so that the total weight of the top plate 420, the tube 425 and the stainless steel weight 415 is 788 g to provide 2.1 kPa of confining pressure during the measurement.

As shown in FIG. 5, bottom plate 405 is approximately 50 mm thick and has two registration grooves 430 cut into the lower surface of the plate such that each groove spans the diameter of the bottom plate and the grooves are perpendicular to each other. Each groove is 1.5 mm wide and 2 mm deep. Bottom plate 405 has a horizontal hole 435 which spans the diameter of the plate. The horizontal hole 435 has a diameter of 11 mm and its central axis is 12 mm below the upper surface of bottom plate 405. Bottom plate 405 also has a central vertical hole 440 which has a diameter of 10 mm and is 8 mm deep. The central hole 440 connects to the horizontal hole 435 to form a T-shaped cavity in the bottom plate 405. The outer portions of the horizontal hole 435 are threaded to accommodate pipe elbows 445 which are attached to the bottom plate 405 in a watertight fashion. One elbow is connected to a vertical transparent tube 460 with a height of 190 mm and an internal diameter of 10 mm. The tube 460 is scribed with a suitable mark 470 at a height of 50 mm above the upper surface of the bottom plate 420. This is the reference for the fluid level to be maintained during the measurement. The other elbow 445 is connected to the fluid delivery reservoir 700 (described below) via a flexible tube.

Figure 6:
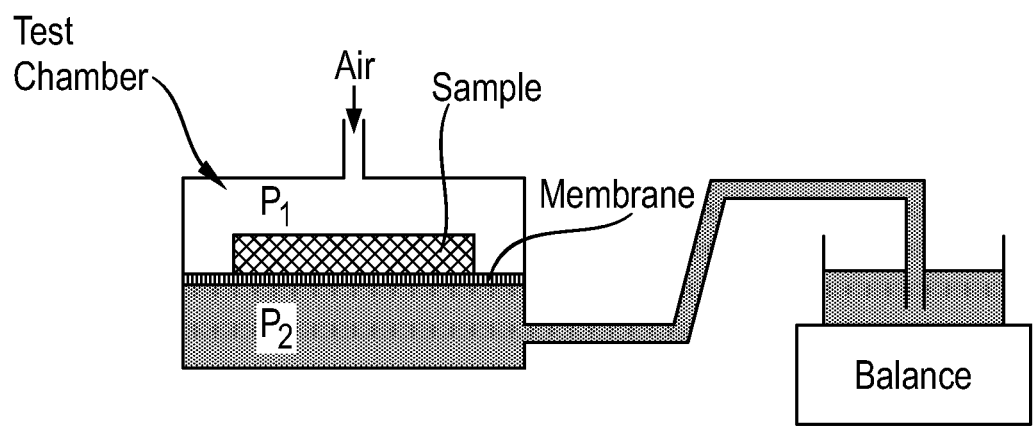
FIG. 6 is a schematic representation of a fluid delivery reservoir for the in plane radial permeability apparatus set up shown in FIG. 4.

A suitable fluid delivery reservoir 700 is shown in FIG. 6. Reservoir 700 is situated on a suitable laboratory jack 705 and has an air-tight stoppered opening 710 to facilitate filling of the reservoir with fluid. An open-ended glass tube 715 having an inner diameter of 10 mm extends through a port 720 in the top of the reservoir such that there is an airtight seal between the outside of the tube and the reservoir. Reservoir 700 is provided with an L-shaped delivery tube 725 having an inlet 730 that is below the surface of the fluid in the reservoir, a stopcock 735, and an outlet 740. The outlet 740 is connected to elbow 445 via flexible plastic tubing 450 (e.g. Tygon®). The internal diameter of the delivery tube 725, stopcock 735, and flexible plastic tubing 450 enable fluid delivery to the IPRP sample holder 400 at a high enough flow rate to maintain the level of fluid in tube 460 at the scribed mark 470 at all times during the measurement. The reservoir 700 has a capacity of approximately 6 liters, although larger reservoirs may be required depending on the sample thickness and permeability. Other fluid delivery systems may be employed provided that they are able to deliver the fluid to the sample holder 400 and maintain the level of fluid in tube 460 at the scribed mark 470 for the duration of the measurement.

The IPRP catchment funnel 500 is shown in FIG. 4 and comprises an outer housing 505 with an internal diameter at the upper edge of the funnel of approximately 125 mm. Funnel 500 is constructed such that liquid falling into the funnel drains rapidly and freely from spout 515. A horizontal flange 520 around the funnel 500 facilitates mounting the funnel in a horizontal position. Two integral vertical internal ribs 510 span the internal diameter of the funnel and are perpendicular to each other. Each rib 510 is 1.5 mm wide and the top surfaces of the ribs lie in a horizontal plane. The funnel housing 500 and ribs 510 are fabricated from a suitably rigid material such as Lexan® or equivalent in order to support sample holder 400. To facilitate loading of the sample it is advantageous for the height of the ribs to be sufficient to allow the upper surface of the bottom plate 405 to lie above the funnel flange 520 when the bottom plate 405 is located on ribs 510. A bridge 530 is attached to flange 520 in order to mount a dial gauge 535 to measure the relative height of the stainless steel weight 415. The dial gauge 535 has a resolution of ±0.01 mm over a range of 25 mm. A suitable digital dial gauge is a Mitutoyo model 575-123 (available from McMaster Carr Co., catalog no. 19975-A73), or equivalent. Bridge 530 has two circular holes 17 mm in diameter to accommodate tubes 425 and 460 without the tubes touching the bridge.

Funnel 500 is mounted over an electronic balance 600, as shown in FIG. 4. The balance has a resolution of ±0.01 g and a capacity of at least 2000 g. The balance 600 is also interfaced with a computer to allow the balance reading to be recorded periodically and stored electronically on the computer. A suitable balance is Mettler-Toledo model PG5002-S or equivalent. A collection container 610 is situated on the balance pan so that liquid draining from the funnel spout 515 falls directly into the container 610.

The funnel 500 is mounted so that the upper surfaces of ribs 510 lie in a horizontal plane. Balance 600 and container 610 are positioned under the funnel 500 so that liquid draining from the funnel spout 515 falls directly into the container 610. The IPRP sample holder 400 is situated centrally in the funnel 700 with the ribs 510 located in grooves 430. The upper surface of the bottom plate 405 must be perfectly flat and level. The top plate 420 is aligned with and rests on the bottom plate 405. The stainless steel weight 415 surrounds the tube 425 and rests on the top plate 420. Tube 425 extends vertically through the central hole in the bridge 530. The dial gauge 535 is mounted firmly to the bridge 530 with the probe resting on a point on the upper surface of the stainless steel weight 415. The dial gauge is set to zero in this state. The reservoir 700 is filled with 0.9% saline solution and re-sealed. The outlet 740 is connected to elbow 445 via flexible plastic tubing 450.

An annular sample 475 of the material to be tested is cut by suitable means. The sample has an outer diameter of 70 mm and an inner hole diameter of 12 mm. One suitable means of cutting the sample is to use a die cutter with sharp concentric blades.

The top plate 420 is lifted enough to insert the sample 475 between the top plate and the bottom plate 405 with the sample centered on the bottom plate and the plates aligned. The stopcock 735 is opened and the level of fluid in tube 460 is set to the scribed mark 470 by adjusting the height of the reservoir 700 using the jack 705 and by adjusting the position of the tube 715 in the reservoir. When the fluid level in the tube 460 is stable at the scribed mark 470 and the reading on the dial gauge 535 is constant, the reading on the dial gauge is noted (initial sample thickness) and the recording of data from the balance by the computer is initiated. Balance readings and time elapsed are recorded every 10 seconds for five minutes. After three minutes the reading on the dial gauge is noted (final sample thickness) and the stopcock is closed. The average sample thickness Lp is the average of the initial sample thickness and the final sample thickness expressed in cm.

The flow rate in grams per second is calculated by linear least squares regression fit to the data between 60 seconds and 300 seconds. The permeability of the material is calculated using the following equation:

Calculation

Data acquisition starts 60 seconds after beginning the test. The software collects the following data at interval of 20 seconds:

Mass of saline in the container on the balance
Thickness of the measured sample
Conductivity or In Plane Radial Permeability (IPRP) $K_r$ is calculated according to Equation #1:

Equation #1:

$$K_r = \frac{k_r}{\mu}$$

Where: $K_r$ is the Conductivity or In Plane Radial Permeability (IPRP)

$k_r$ is the permeability according to Equation #2
$\mu$ is the liquid dynamic viscosity of saline 0.9% (value used here: 0.001 Pa*s)

Equation #2:

$$k_r = \frac{\sum_{i=1}^{max} k_{r,i}}{max}$$

Where: $k_{r,i}$ is the permeability at time i according to Equation #3
max is the number of acquired data points Equation #3:

$$k_{r,i} = \frac{(Q_i/\rho) * \mu * \ln(R_o/R_m)}{2\pi * Lp_i * p_i}$$

Where:
$Q_i$ is the mass flow rate at time i according to equation #4
$\rho$ is the density of 0.9% saline (value used here 1.01 g/cm3)
$\mu$ is the liquid dynamic viscosity at 20° C.

$R_o$ is the outer sample radius.
$R_m$ is the inner sample radius.
$L_{p_i}$ is the averaged sample thickness for time i according to Equation #5
$\Delta_{p_i}$ is the pressure drop calculated according to Equation #6:

Equation #4:

$$Q_{(i)} = \frac{(g_{(i)} - g_{(i-1)})}{(t_{(i)} - t_{(i-1)})}$$

Where:
$t_{(i)}$ is the time i
$g_{(i)}$ is the fluid mass measured by the balance at time i
i is the index Equation #5:

$$Lp_i = \frac{(lp_{(i)} + lp_{(i-1)})}{2}$$

Where:
$l_{p_i}$ is the sample thickness at time i (TMM software averages the readings of the two caliper gauges).

Equation #6:

$$\Delta p_i = \left(\Delta P - \frac{Lp_i}{2}\right) * g * \rho$$

Where:
g is the acceleration gravity (value used here: 9.81 m/s2)
ΔP is the hydrostatic head as displayed in the glass tube. Note that the hydrostatic head is of dimension length.

Air Permeability

Air permeability is measured in accordance with Edana standard test method WSP 70.1 (08).

TEXTEST FX 3300 Air Permeability Tester apparatus or equivalent is used.

Test Head Model FX 3300-20 or equivalent is used. An area of 20 cm² is tested.

The pressure drop is set to 125 Pa, orifice area is 38.3 cm².

The instrument is calibrated according to manufacturer's instruction, and test is performed as specified in manufacturer's instructions.

Testing is performed in a conditioned room maintained at 23° C.±2° C. and 50% RH±2%.

EXAMPLES

Example 1: Through Air Bonded Nonwoven Fibrous Web with Latex Binder

The fibrous web has a basis weight of 60 g/m² and consists of 80% by weight of staple fibers (48 g/m²) and 20% of latex binder (12 g/m²). The staple fibers are a mixture of 6 denier solid round PE/PET concentric sheath/core bicomponent fibers (i.e. sheath made of polyethylene and core made of polyethylene terephthalate) and 1.2 denier solid trilobal PET monocomponent fibers. The mixture consists of 80%, by total weight of the staple fibers, of bicomponent fibers and 20%, by total weight of the staple fibers, of trilobal monocomponent fibers.

The bicomponent fibers are commercially available from FiberVisions Corp. under the name ETC267CG3. The monocomponent fibers are commercially available from Kilop USA Inc. under the name Tarilin Nan Ya Y01. The latex binder is supplied by Omnova Solutions Inc. under the name Genflow 3160.

The mixture of staple fibers was laid down and underwent an air-through bonding step. An air-through bonder was used where the fibrous layer passes over a drum inside a hood, as exemplary shown in FIG. 3). The temperature in the bonder was set at 130° C. The fibrous layer traveled at a speed of 14.3 m/min with a residual time in the bonder of about 35 seconds. Subsequently, the latex binder was homogeneously applied onto the web by passing the web through a bath which contained the liquid latex binder (aqueous suspension with 20% binder) and the web was then subjected to curing by passing the web over drying cans at a temperature of about 150° C. to 170° C. and thereafter passing the web through an oven at 180° C. to obtain the final web. Residual time in the oven was about 40 seconds. The web traveled at a speed of 13.9 m/min.

Comparative Example 1: Through Air Bonded Nonwoven Fibrous Web without Latex Binder The fibrous web consists of 100% by weight of staple fibers (60 g/m$^2$). The staple fibers are a mixture of 6 denier solid round PE/PET concentric sheath/core bicomponent fibers (i.e. sheath made of polyethylene and core made of polyethylene terephthalate) and 1.2 denier solid trilobal PET monocomponent fibers. The mixture consists of 80%, by total weight of the staple fibers, of bicomponent fibers and 20%, by total weight of the staple fibers, of trilobal monocomponent fibers.

The bicomponent fibers are commercially available from FiberVisions Corp. under the name ETC267CG3. The monocomponent fibers are commercially available from Kilop USA Inc. under the name Tarilin Nan Ya Y01.

The mixture of staple fibers was laid down and underwent an air-through bonding step. An air-through bonder was used where the fibrous layer passes over a drum inside a hood, as exemplary shown in FIG. 3). The temperature in the bonder was set at 130° C. The fibrous layer traveled at a speed of 14.3 m/min with a residual time in the bonder of about 35 seconds.

Example 2: Through Air Bonded Nonwoven Fibrous Web with Latex Binder

The fibrous web consists of 80% by weight of staple fibers (48 g/m$^2$) and 20% of latex binder (12 g/m$^2$). The staple fibers are a mixture of 6 denier solid round CoPET/PET concentric sheath/core bicomponent fibers (i.e. sheath made of CoPET and core made of polyethylene terephthalate) and 1.2 denier solid trilobal PET monocomponent fibers. The mixture consists of 80%, by total weight of the staple fibers, of bicomponent fibers and 20%, by total weight of the staple fibers, of trilobal monocomponent fibers.

The bicomponent fibers are commercially available from Toray Chemical Int. under the name Eslom UL007. The monocomponent fibers are commercially available from Kilop USA Inc. under the name Tarilin Nan Ya Y01. The latex binder is supplied by Omnova Solutions Inc. under the name Genflow 3160.

The mixture of staple fibers was laid down and underwent an air-through bonding step. An air-through bonder was used where the fibrous layer passes over a drum inside a hood, as exemplary shown in FIG. 3). The temperature in the bonder was set at 150° C. The fibrous layer traveled at a speed of 14.2 m/min with a residual time in the bonder of about 35 seconds. Subsequently, the latex binder was homogeneously applied onto the web by passing the web through a bath which contained the liquid latex binder (aqueous suspension with 20% binder) and the web was then subjected to curing by passing the web over drying cans at a temperature of about 150° C. to 170° C. and thereafter passing the web through an oven at 180° C. to obtain the final web. Residual time in the oven was about 40 seconds. The web traveled at a speed of 13.9 m/min.

Comparative Example 2: Through Air Bonded Nonwoven Fibrous Web with Latex Binder The fibrous web consists of 100% by weight of staple fibers (60 g/m$^2$). The staple fibers are a mixture of 6 denier solid round CoPET/PET concentric sheath/core bicomponent fibers (i.e. sheath made of CoPET and core made of polyethylene terephthalate) and 1.2 denier solid trilobal PET monocomponent fibers. The mixture consists of 80%, by total weight of the staple fibers, of bicomponent fibers and 20%, by total weight of the staple fibers, of trilobal monocomponent fibers.

The bicomponent fibers are commercially available from Toray Chemical Int. under the name Eslom UL007. The monocomponent fibers are commercially available from Kilop USA Inc. under the name Tarilin Nan Ya Y01.

The mixture of staple fibers was laid down and underwent an air-through bonding step. An air-through bonder was used where the fibrous layer passes over a drum inside a hood, as exemplary shown in FIG. 3). The temperature in the bonder was set at 150° C. The fibrous layer traveled at a speed of 14.2 m/min with a residual time in the bonder of about 35 seconds.

TABLE 1

Results

| | Example 1 | Comparative Example 1 | Example 2 | Comparative Example 2 |
|---|---|---|---|---|
| Caliper Recovery after Compression at 12 kPa [%] | 68.3 | 63.6 | 58.4 | 53.0 |
| Caliper Recovery after Compression at 4 kPa [%] | 84.5 | 82.4 | 79.7 | 69.4 |
| Caliper Recovery after Compression at 1 kPa [%] | 96.9 | 93.5 | 96.7 | 87.6 |
| Air Permeability before compression [m$^3$/m$^2$/min] | 333 | 246 | 315 | 303 |
| IPRP before compression [10$^6$ (cm/Pa sec)] | 16,874 | 12,696 | 21,208 | 19,293 |
| IPRP 24 h after compression at 4 kPa [10$^6$ (cm/Pa sec)] | 13,384 | 10,180 | 21,368 | 16,783 |

The data show that by subjected to air-through bonded carded nonwoven fibrous web to subsequent treatment with a latex binder and curing the web, the Caliper Recovery after compression at 12 kPa improves by 7% for Example 1 vs. Comparative Example 1, and by 10% for Example 2 vs. Comparative Example 2.

Caliper Recovery after compression at 4 kPa improves by 2.5% for Example 1 vs. Comparative Example 1, and by 15% for Example 1 vs. Comparative Example 1.

Caliper Recovery after compression at 1 kPa improves by 4% for Example 1 vs. Comparative Example 1, and by 10% for Example 2 vs. Comparative Example 2.

Also Air Permeability (measured without having the carded nonwoven fibrous web subjected to compression) and In Plane Radial Permeability (IPRP) (measured without having the carded nonwoven fibrous webs subjected to compression prior to testing as well as measured for the webs 24 h after they were compressed at 4 kPa) is improved with additional treatment with a latex binder:

Air Permeability increases by 35% for Example 1 vs. Comparative Example 1, and by 4% for Example 2 vs. Comparative Example 2.

IPRP increases by 33% for Example 1 vs. Comparative Example 1, and by 10% for Example 2 vs. Comparative Example 2 for the webs without previous compression. IPRP increases by 31% for Example 1 vs. Comparative Example 1, and by 27% for Example 2 vs. Comparative Example 2 for the webs 24 h after they were compressed at 4 kPa.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A carded nonwoven fibrous web comprising about 50% to about 90%, by weight of the fibrous web, of staple fibers and at least 10%, by weight of the fibrous web, of non-fibrous latex binder, wherein the staple fibers are autogenously bonded to each other and are bonded to each other by the latex binder, wherein autogenous bonding of the staple fibers was carried out prior to application of the latex binder, wherein the fibrous web comprises a mixture of at least a first and a second type of the staple fibers, wherein the first type of the staple fibers are multicomponent fibers having a denier of from about 4 denier to about 10 denier, and wherein the second type of the staple fibers are monocomponent fibers having a denier of from about 0.8 denier to 2.5 denier.

2. The carded nonwoven fibrous web of claim 1, wherein the staple fibers comprise at least 20%, by total weight of the staple fibers, of multicomponent fibers.

3. The carded nonwoven fibrous web of claim 2, wherein the multicomponent fibers are core/sheath bicomponent fibers.

4. The carded nonwoven fibrous web of claim 1, wherein the staple fibers comprise at least 5%, by total weight of the staple fibers, of non-round shaped fibers.

5. The carded nonwoven fibrous web of claim 1, wherein the fibrous web has a basis weight of from about 20 $g/m^2$ to about 100 $g/m^2$.

6. The carded nonwoven fibrous web of claim 1, wherein the staple fibers are made of polypropylene, polyethylene, polyester, polyethylene terephthalate (PET), CoPET, polybutylene terephthalate, polyamide, polylactic acid, viscose, and combinations thereof.

7. The carded nonwoven fibrous web of claim 1, wherein the fibrous web comprises from about 65% to about 95%, by total weight of the staple fibers, of the first type of fibers and from about 5% to about 35%, by total weight of the staple fibers, of the second type of fibers.

8. The carded nonwoven fibrous web of claim 1, wherein the latex binder is a styrene-butadiene copolymer binder.

9. The carded nonwoven fibrous web of claim 1, wherein the caliper recovery after compression at 12 kPa increases by at least 5%, or at least 7%, compared to a comparative carded nonwoven fibrous web, which has the same fiber composition as the carded nonwoven fibrous web but does not comprise any binder.

10. The carded nonwoven fibrous web of claim 1, wherein the In Plane Radial Permeability increases by at least 10%, or at least 20%, compared to a comparative carded nonwoven fibrous web, which has the same fiber composition as the carded nonwoven fibrous web but does not comprise any binder.

11. An absorbent article comprising the carded nonwoven fibrous web of claim 1.

12. The absorbent article of claim 11, wherein the absorbent article comprises a topsheet, a backsheet and an absorbent core disposed at least partially between the topsheet and the backsheet, and wherein the absorbent article comprises an acquisition system disposed at least partially between the absorbent core and the topsheet, the acquisition system comprising the carded nonwoven fibrous web.

13. A carded nonwoven fibrous web comprising about 50% to about 90%, by weight of the fibrous web, of staple fibers and at least 10%, by weight of the fibrous web, of non-fibrous latex binder, wherein the staple fibers are autogenously bonded to each other and are separately and subsequently bonded to each other by the latex binder, wherein the fibrous web comprises a mixture of at least a first and a second type of the staple fibers, wherein the first type of the staple fibers are multicomponent fibers having a denier of from about 4 denier to about 10 denier, and wherein the second type of the staple fibers are monocomponent fibers having a denier of from about 0.8 denier to 2.5 denier.

14. The carded nonwoven fibrous web of claim 13, wherein the staple fibers comprise at least 20%, by total weight of the staple fibers, of multicomponent fibers.

15. The carded nonwoven fibrous web of claim 14, wherein the multicomponent fibers are core/sheath bicomponent fibers.

16. The carded nonwoven fibrous web of claim 15, wherein the staple fibers comprise at least 5%, by total weight of the staple fibers, of multilobal fibers.

17. The carded nonwoven fibrous web of claim 16, wherein the fibrous web has a basis weight of from about 20 g/m² to about 100 g/m².

18. A carded nonwoven fibrous web comprising about 50% to about 90%, by weight of the fibrous web, of staple fibers and at least 15%, by weight of the fibrous web, of non-fibrous latex binder, wherein the staple fibers are autogenously bonded to each other and are separately and subsequently bonded to each other by the latex binder, and wherein the staple fibers comprise at least 20%, by total weight of the staple fibers, of multicomponent fibers, wherein the fibrous web comprises a mixture of at least a first and a second type of the staple fibers, wherein the first type of the staple fibers are multicomponent fibers having a denier of from about 4 denier to about 10 denier, and wherein the second type of the staple fibers are monocomponent fibers having a denier of from about 0.8 denier to 2.5 denier.

* * * * *